(12) United States Patent
Huang et al.

(10) Patent No.: US 10,964,195 B1
(45) Date of Patent: Mar. 30, 2021

(54) METHOD AND SYSTEM OF ALERTING PATIENT WITH SLEEP DISORDER

(71) Applicants: Lina Huang, San Dimas, CA (US); Kelly Huang, San Dimas, CA (US)

(72) Inventors: Lina Huang, San Dimas, CA (US); Kelly Huang, San Dimas, CA (US)

( * ) Notice: Subject to any disclaimer, the term of this patent is extended or adjusted under 35 U.S.C. 154(b) by 0 days.

(21) Appl. No.: 16/734,355

(22) Filed: Jan. 5, 2020

(51) Int. Cl.
```
G08B 23/00      (2006.01)
G08B 21/18      (2006.01)
A61B 5/00       (2006.01)
A61B 5/0205     (2006.01)
A61B 5/11       (2006.01)
G08B 3/10       (2006.01)
A61B 5/021      (2006.01)
A61B 5/08       (2006.01)
A61B 5/024      (2006.01)
```

(52) U.S. Cl.
CPC .......... *G08B 21/182* (2013.01); *A61B 5/0205* (2013.01); *A61B 5/1118* (2013.01); *A61B 5/4818* (2013.01); *A61B 5/6801* (2013.01); *A61B 5/741* (2013.01); *A61B 5/746* (2013.01); *A61B 5/7415* (2013.01); *G08B 3/10* (2013.01); *A61B 5/021* (2013.01); *A61B 5/024* (2013.01); *A61B 5/0816* (2013.01); *A61B 2562/0204* (2013.01); *A61B 2562/0219* (2013.01)

(58) Field of Classification Search
CPC ...... G08B 21/182; G08B 3/10; A61B 5/0205; A61B 5/1118; A61B 5/4818; A61B 5/6801; A61B 5/741; A61B 5/7415; A61B 5/746; A61B 5/021; A61B 5/024; A61B 5/0816; A61B 2562/0204; A61B 2562/0219

USPC .......................................................... 340/575
See application file for complete search history.

(56) References Cited

U.S. PATENT DOCUMENTS

| | | | |
|---|---|---|---|
| 9,211,411 B2 * | 12/2015 | Wu .................... | A61B 5/4815 |
| 2005/0042589 A1 * | 2/2005 | Hatlestad ............. | A61B 5/0031 434/262 |
| 2005/0258973 A1 * | 11/2005 | Black ...................... | G08B 3/10 340/628 |
| 2007/0055115 A1 * | 3/2007 | Kwok .................. | A61B 5/0205 600/300 |
| 2007/0173728 A1 * | 7/2007 | Pu ....................... | A61B 5/02405 600/484 |
| 2007/0239057 A1 * | 10/2007 | Pu ........................ | A61B 5/4818 600/529 |
| 2009/0192556 A1 * | 7/2009 | Wu ...................... | A61B 5/4839 607/3 |
| 2011/0006901 A1 * | 1/2011 | Cassidy ............. | A61B 5/14551 340/573.1 |
| 2011/0190594 A1 * | 8/2011 | Heit ..................... | A61B 5/4815 600/301 |

(Continued)

*Primary Examiner* — Kerri L McNally
*Assistant Examiner* — Thang D Tran

(57) ABSTRACT

A method and a system of alerting patient with sleep disorder are provided. The method includes: detecting a change in a parameter(s), and if the change is detected, sounding an alarm, wherein the parameter(s) includes sound, motion, heartbeat, blood pressure, breathing frequency, magnitude and/or frequency of movement. The system includes a detector for detecting a change in a parameter(s) and an output device for sounding an alarm, wherein the parameter(s) comprise(s) sound, motion, heartbeat, blood pressure, breathing frequency, and/or magnitude and/or frequency of movement.

20 Claims, 3 Drawing Sheets

Detecting a change in a parameter

↓

Sounding an alarm

(56) References Cited

U.S. PATENT DOCUMENTS

| | | | | |
|---|---|---|---|---|
| 2011/0253884 A1* | 10/2011 | Ottleben | ................... | G01V 8/20 |
| | | | | 250/221 |
| 2012/0092171 A1* | 4/2012 | Hwang | ............... | G06F 19/3481 |
| | | | | 340/575 |
| 2012/0253142 A1* | 10/2012 | Meger | .................. | A61B 5/7415 |
| | | | | 600/301 |
| 2014/0278139 A1* | 9/2014 | Hong | ................... | A61B 5/7264 |
| | | | | 702/19 |
| 2014/0350355 A1* | 11/2014 | Aisic | ........................ | A61B 7/04 |
| | | | | 600/301 |
| 2015/0148857 A1* | 5/2015 | Macho | .................. | A61N 1/0484 |
| | | | | 607/7 |
| 2015/0150498 A1* | 6/2015 | George | ................ | A61B 5/4818 |
| | | | | 600/301 |
| 2015/0150499 A1* | 6/2015 | George | ................ | A61B 5/4818 |
| | | | | 600/301 |
| 2015/0150501 A1* | 6/2015 | George | ................ | A61B 5/6817 |
| | | | | 600/301 |
| 2015/0310718 A1* | 10/2015 | Wilson | ............... | A61M 16/0051 |
| | | | | 340/632 |
| 2015/0343130 A1* | 12/2015 | Rosa-Bray | .......... | A61M 1/3496 |
| | | | | 210/651 |
| 2016/0015314 A1* | 1/2016 | Dusanter | ............. | A61B 5/0816 |
| | | | | 600/301 |
| 2016/0015315 A1* | 1/2016 | Auphan | ............... | A61B 5/6892 |
| | | | | 600/301 |
| 2016/0022193 A1* | 1/2016 | Rau | ........................ | A61B 5/165 |
| | | | | 600/301 |
| 2016/0140827 A1* | 5/2016 | Derenne | ................ | A61B 5/747 |
| | | | | 340/573.7 |
| 2016/0317781 A1* | 11/2016 | Proud | .................... | A61B 5/165 |
| 2017/0020443 A1* | 1/2017 | Fein | ........................ | G16H 40/63 |
| 2017/0112671 A1* | 4/2017 | Goldstein | ............ | H04R 25/554 |
| 2017/0135632 A1* | 5/2017 | Franceschetti | ......... | A61G 7/002 |
| 2017/0347950 A1* | 12/2017 | Jones | ..................... | A61B 5/746 |
| 2018/0110463 A1* | 4/2018 | Dai | ........................ | A61B 5/0205 |
| 2018/0125256 A1* | 5/2018 | Tsern | .................... | G05B 13/024 |
| 2018/0133480 A1* | 5/2018 | Annoni | .............. | A61N 1/36117 |
| 2019/0008450 A1* | 1/2019 | Gurievsky | ........... | A61B 5/1135 |
| 2019/0008577 A1* | 1/2019 | Lazarus | .............. | A61B 5/4815 |
| 2019/0223781 A1* | 7/2019 | Arrington | ............ | A61B 5/0022 |
| 2020/0077892 A1* | 3/2020 | Tran | ..................... | A61B 5/6824 |
| 2020/0129528 A1* | 4/2020 | Barbut | .................. | A61K 35/60 |
| 2020/0187860 A1* | 6/2020 | Myslinski | ........... | A61B 5/4839 |
| 2020/0335211 A1* | 10/2020 | Gopalakrishnan | ... | A61B 5/4809 |

\* cited by examiner

METHOD AND SYSTEM OF ALERTING PATIENT WITH SLEEP DISORDER

FIELD

The present disclosure is related to a method and a system of alerting patient(s) with sleep disorder.

BACKGROUND

Patients with sleep disorder, such as rapid eye movement sleep behavior disorder (RBD) or sleep terror, have the potential to be injured or have disrupted sleep behavior, indicated by talking, laughing, shouting, gesturing, grabbing, flailing arms, punching, kicking, sitting up, and/or leaping from bed. Sometimes vigorous, violent episodes may occur.

For example, RBD is typically characterized by abnormal or disruptive behaviors emerging during the rapid eye movement (REM) sleep stage. Most people are paralyzed during this sleep period; however, RBD patients are not and therefore can act out their dreams. These actions can include shouting, kicking, running, etc., which may cause serious injury and/or harm to themselves, and/or disruptions to others nearby (e.g., sleep partners).

In contrast to sleep walking, patients with RBD can be easily woken up with even small noises. However, many RBD patients live alone, and may not be able to be alerted until injured by their movements.

The medical treatments for RBD (e.g., medications) are not always effective, and may also have undesirable side effects.

Also, for example, in patients with obstructive sleep apnea (OSA), the soft tissue in the back of the throat collapses and blocks the airway, which leads to partial reductions in breathing, commonly referred to as "hypopneas". This can lead to complete pauses in breathing, which are often referred to as "apneas." In children, these obstructions tend to occur during the rapid eye movement (REM) sleep stage. OSA may cause the patient to have low levels of oxygen in the blood. While adults with OSA may wake up easily after their breathing stops, children with OSA often do not wake up in response to pauses in breathing. OSA may lead to deformation of the chest, such as depression in the chest wall, abnormal sleep positions, and other health issues and/or behavior issues. For example, patients with OSA may suffer from high blood pressure, heart disease, stroke, prediabetes and diabetes, and depression.

As such, there is a need for helping patients with sleep disorder, such as RBD or OSA, to avoid harm or injury.

SUMMARY

An aspect of the present disclosure is directed toward a method of alerting a patient with sleep disorder, for example, patient with rapid eye movement (REM) sleep behavior disorder (RBD).

Another aspect of the present disclosure is directed toward a system for alerting a patient with sleep disorder, e.g., an RBD patient.

Other aspects will be set forth in the descriptions below, and will be clear from the description, or may be learned by practice of the presented embodiments.

According to an embodiment, a method of alerting, preventing injury, and/or monitoring of patient(s) with sleep disorder includes: detecting a change in a parameter(s), and if the change is detected, sounding an alarm, wherein the parameter(s) includes sound, motion, heartbeat, blood pressure, breathing frequency, magnitude and/or frequency of movement.

This method aids in preventing the patient from injury and/or harm in that it senses parameters indicative of injury-causing actions and alerts the patient before those actions occur (e.g., before the patient leaves the bed).

The method may further include deciding if the change meets a set criteria, and if the change meets the set criteria, sounding the alarm.

The set criteria may be adaptable to sleep behavior of the patient.

The parameter may be sound, and the set criteria may include a pitch and/or volume of the sound.

The parameter may be motion, and the set criteria may include a range, speed, and/or a frequency of the motion.

The parameter may be heartbeat, and the set criteria may include a threshold value of the heartbeat.

The parameter may be blood pressure, and the set criteria may include a threshold value of the blood pressure.

The parameter may be magnitude and/or frequency of movement, and the set criteria may include a threshold value of the magnitude and/or frequency of movement.

The parameter may be breathing frequency, and the set criterial may include an interval between adjacent breathes.

The method may further include detecting a time duration of the change in the parameter, and the set criteria may include a threshold value of the time duration.

The alarm may include a customizable message.

The method may further include establishing a customized reference value for the parameter for an individual (e.g., a specific) patient.

The method may further include attaching a device to the patient, wherein the device is to detect the parameter and/or sound the alarm.

According to an embodiment, a system of alerting/preventing injury and/or monitoring of patient with sleep disorder, such as RBD, includes a detector for detecting a change in a parameter(s) and an output device for sounding an alarm, wherein the parameter(s) comprise(s) sound, motion, heartbeat, blood pressure, breathing frequency, and/or magnitude and/or frequency of movement.

The system may further include a control unit for deciding if the change meets a set criteria, and if the change meets the set criteria, sounding the alarm.

The detector may be a heartbeat monitor, a motion sensor, an audio detector, and/or a blood pressure sensor.

The control unit may adapt the set criteria according to sleep behavior of the patient.

The control unit may include a codable device.

The control unit may communicate with a remote device (e.g., a smartphone, a smartwatch, a laptop).

The remote device may have a customizable program to display data, set values, track history, and/or communicate with other devices.

The output device may be a speaker and/or vibrating device. The output device may be customizable (e.g., message, volume, duration, tone).

DETAILED DESCRIPTION

According to embodiments of the present disclosure, a method and a system of alerting patient with sleep disorder are provided.

Figure 1:
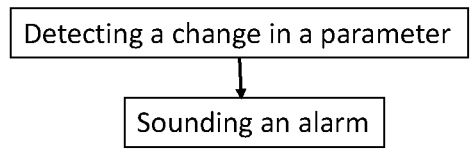
FIG. 1 is a flow chart illustrating a method of alerting a patient with sleep disorder according to an embodiment of the present disclosure.
Figure 2:
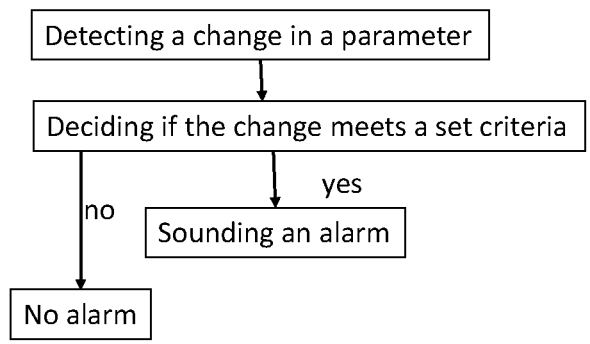
FIG. 2 is a flow chart illustrating a method of alerting a patient with sleep disorder according to an embodiment of the present disclosure.

FIGS. 1 and 2 are each a flow chart illustrating a method of alerting a patient with sleep disorder. Referring to FIG. 1, according to an embodiment, a method of alerting, preventing injury and/or monitoring a patient with sleep disorder, such as RBD includes: detecting a change in a parameter(s) and sounding an alarm, wherein the parameter(s) includes sound, motion, heartbeat, blood pressure, breathing frequency, magnitude and/or frequency of movement.

Referring to FIG. 2, the method may further include deciding if the change meets a set criteria, and if the change meets the set criteria, sounding the alarm.

During sleep, the patient (e.g., an RBD patient) may have a dream (e.g., nightmare) in which the patient may act out the dream, using hands and arms for dramatic motions, speaking in relation to the dream scene, and/or rolling or jumping off the bed. Without being conscious of their surroundings, they may bump into things such as the bed frames, other furniture around them, doors, fall into bath tubs, and/or disrupt others nearby.

To avoid patient injury, a detector (e.g., a sensor, a monitoring device, etc.) may be utilized to detect and/or monitor the parameters that change or manifest during times of abnormal action in sleep, such as sound (e.g., shouting, yelling, crying, etc., of the patient), motion (e.g., waving of the arms, kicking, turning the body, etc.), heartbeat, blood pressure, breathing frequency, magnitude and/or frequency of movement (e.g., of arms, legs, head, etc.), etc.

The detector may be installed at a location near the patient, such as on the wall near the bed, on the bed (e.g., bed frame), coupled to a smartphone, or may be a wearable device worn on the patient (e.g., wrist, arm, ankle, legs, feet, hand, head, ear, etc.), or attached to the patient (e.g., through pajamas, socks, etc.).

The parameter may be sound, and the set criteria may include pitch, frequency, intensity, and/or volume of the sound. For example, when the patient starts screaming or talking excitedly, the detector may detect the pitch, frequency, intensity, and/or volume (e.g., the change in the pitch, frequency, intensity, and/or volume from prior to the screaming or talking). Furthermore, the detected pitch, frequency, intensity, and/or volume of sound may be compared with a set criteria, such as the pitch, frequency, intensity, and/or volume of normal speaking voice of the patient, and/or normal snoring sound of the patient. If the detected pitch, frequency, intensity, and/or volume exceeds the set criteria, the patient alert system may sound an alarm to wake the patient. For example, if the patient screams, the system will detect the change in the sound, e.g., increased volume, shifting of sound frequency and/or pitch from the normal speaking voice of the patient, and activate the alarm.

In one embodiment, the patient alert system including the detector may take the normal snoring sound and normal (peaceful) speaking sound of the patient as the baseline sound. The system may be set so that the set criteria is above the baseline sound of the patient with an adaptable tolerance. Accordingly, the system may not sound the alarm when no change that meet the set criteria (e.g., no sound that exceeds the baseline sound) is detected. In this case, the normal sleep talking (e.g., non-violent episodes) or snoring will not trigger the alarm.

In one embodiment, the sensitivity of the detector may be set to be above the baseline sound, such that the alarm will sound only when the sound exceeds the baseline sound in one or more of the pitch, frequency, intensity, volume, etc.

The set criteria may be customized according to the habits and/or normal state of the patient, and may be determined based on the individual symptoms so that the alarm will sound when the patient's dream has progressed to injury-causing scenarios, but it will not sound when the patient is dreaming in a peaceful manner that will not lead to dangerous episodes. For example, the patient alert system may have a number of trigger levels, and the patient and/or caregiver may choose the trigger level through trial and error and/or by measuring/observing the patient's states.

The parameter may be motion, and the set criteria may include a speed and/or a frequency of the motion. For example, when the system detects the patient waving their arms and/or kicking violently (e.g., at a frequency, range, or magnitude above normal sleep activity), it may sound the alarm. However, movements that are not likely to cause harm and/or injury to the patient (e.g., peacefully switching sides, occasional turning) during sleep may not trigger the alarm.

The parameter may be heartbeat, and the set criteria may include a threshold value. For example, when the patient moves their arms and/or legs violently or when the patient dreams of a violent scenario, their heartbeat may be significantly higher than the normal rate of heartbeat during sleep. The set criterial may be a heartbeat value that is higher (e.g., 10%, 20%, or 30% more and/or 10 beats per minute, 20 beats per minute, or 30 beats per minute more) than the normal sleep heartbeat.

The parameter may be blood pressure, and the set criteria may include a threshold value. The blood pressure may be monitored through a blood pressure gauge on the patient (e.g., on the wrist), and the threshold value may be significantly higher than the normal blood pressure of the patient, such as 3%, 5%, 10% or 15% higher. This gauge may measure the systolic pressure, diastolic pressure, or both. The alarm may be integrated with the blood pressure gauge, or may be separate and/or located at a location different from the blood pressure gauge.

The parameter may be breathing frequency, and the set criteria may include a threshold value. For example, if the patient is breathing above the threshold frequency, such as an increased rate of 10%, 15%, 20%, etc., the increased frequency may trigger the alarm.

The parameter may be magnitude and/or frequency of the movement, and the set criteria may include a threshold value. For example, if the patient waves arms or kicks legs 2 times or more in a set time frame, such as 10 seconds, 30 seconds, 1 minute, etc., the increased frequency of movement may trigger the alarm.

The parameter may be the orientation of the patient's body. For example, when the patient changes from one lying position to another position that is 15° or more in angle from the original lying position, or change from a lying position to sitting up or standing position, the sensor may sense the change in the body orientation and trigger the alarm.

In one embodiment, two or more of the parameters may be utilized together. For example, two or more selected from sound (e.g., shouting, yelling, crying, etc., of the patient), motion (e.g., waving of the arms, punching, kicking, fast turning of the body, standing, etc.), heartbeat, blood pressure, breathing frequency, and magnitude and frequency of movement (e.g., of arms, legs, head, etc.) are utilized together in detecting the state of the patient in sleep and the controller triggers the alarm based on the two or more detected parameters.

The method may further include detecting a time duration of the change in the parameter, and the set criteria may include a threshold value of the time duration. For example, when the patient toss and turns for a set time duration, the alarm may sound. In one embodiment, even when the movement is in a smaller magnitude, if the movement happens more than a set number during a set period, the alarm may sound. For example, if the motion happens more than three times in 5 seconds, 10 seconds, etc., the alarm will sound.

In one embodiment, for a patient with OSA, the parameter may be breathing frequency and the set criteria may include a reduction in the breathing frequency. If the patient has stopped breathing for a set period of time, such as 5 seconds, 10 seconds, etc., the alarm may sound.

The alarm may include a customizable message. The customizable message may be a desired message for the patient, such as a close family member's voice saying "wake up," "mom," "dad," etc. The customizable message may also be a phrase chosen by the patient, such as one from a favorite song lyric, a phrase from the Bible, a movie line, etc.

In another embodiment, the alarm may be physical vibration, or both physical vibration and sound. The alarm may be included in a wearable device such that when triggered, the physical vibration can provide the stimulation to wake up the patient.

The method may further include establishing a reference (e.g., a baseline) value for the parameter for a specific patient. For example, the patient and/or caregiver may monitor the symptoms of the patient and establish the correlation between the voice, motion, heartbeat, blood pressure, magnitude and/or frequency of movement and the likelihood of the patient engaging in endangering actions, such as jumping off the bed, falling off the bed, hitting the bed frame, etc. This may also include symptoms of the patient that establish the correlation between the voice, motion, heartbeat, blood pressure, breathing frequency, magnitude and/or frequency of movement and the likelihood of the patient engaging in disruptive actions, such as shouting, pounding on the bed, etc. The set criteria can then be established so that it will accurately indicate the endangering actions before the patient actually hurt himself/herself.

The method may further include putting a device on the patient, wherein the device is to detect the parameter(s) and/or sound the alarm. For example, the device may be put on the patient's wrists, ankles, arms, legs, forehead, etc., through a belt, wrist band, or through attachment to socks, gloves, pajamas, eye mask, hairband, etc.

FIGS. 3A-3D schematically show a method of alerting a patient with sleep disorder according to an embodiment of the present disclosure.

Figure 3A:
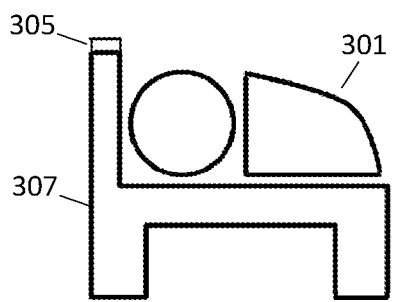
FIGS. 3A-3D schematically show a method of alerting a patient with sleep disorder according to an embodiment of the present disclosure.
Figure 3B:
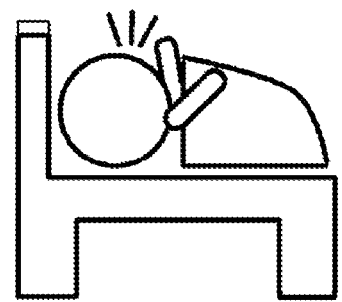
Figure 3C:
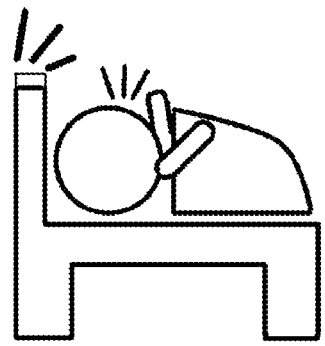
Figure 3D:
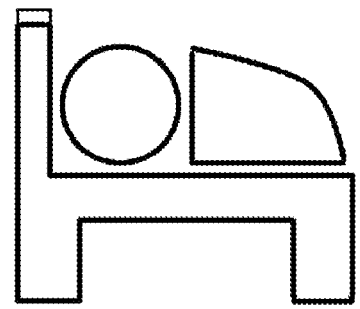

Referring to FIGS. 3A-3D, the patient 301 initially sleeps peacefully in bed 307, and the patient alert system 305 does not sound any alarm (FIG. 3A). The patient 301 then starts making moves (e.g., waving arms) and/or shouting during an abnormal sleep stage (FIG. 3B). The change in the motion and/or sound is detected by the detector of the patient alert system 305 near the patient 301, and the patient alert system 305 sounds an alarm (FIG. 3C) to wake the patient 301 from sleep to avoid the patient from hurting himself/herself with more violent moves, jumping off the bed, etc. Once the patient is awake, the patient resets the alarm and falls back to a peaceful sleep (FIG. 3D).

Figure 4:
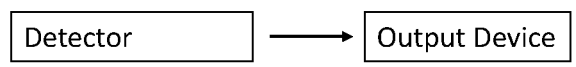
FIG. 4 is a schematic illustration of a system for altering a patient with sleep disorder according to an embodiment of the present disclosure.
Figure 5:
FIG. 5 is a schematic illustration of a system for altering a patient with sleep disorder according to an embodiment of the present disclosure.

FIGS. 4 and 5 are each a schematic illustration of a system for altering a patient with sleep disorder. Referring to FIG. 4, according to an embodiment, a system of alerting, preventing injury and/or monitoring of patient with sleep disorder, such as RBD, includes a detector for detecting a change in a parameter(s) and an output device for making an alarm, wherein the parameter(s) comprises sound, motion, heartbeat, blood pressure, breathing frequency, magnitude and/or frequency of movement.

Referring to FIG. 5, the system may further include a control unit for deciding if the change meets a set criteria, and if the change meets the set criteria, triggering the output device to sound the alarm.

The detector may be a heartbeat detector (heartbeat monitor), a motion detector (motion sensor, Passive Infrared (PIR) sensor, etc.), a sound detector (an audio sensor, a microphone, etc.), an accelerometer (tilt sensor), a global positioning system (GPS), an optical heart rate monitor, a thermometer, a bioimpedance sensor, and/or a blood pressure sensor. However, the present disclosure is not limited thereto, and any suitable sensor for sensing the related parameters may be utilized in the system according to embodiments of the present disclosure.

The control unit may include a central processor unit (CPU), a codable device, etc. For example, the control unit may be an Arduino board, a Raspberry Pi, an integrated circuit board, or any suitable processor where the input is a signal from the detector, and the output is the alarm. The control unit may be programmed utilizing any suitable programming language, such as Python, Java, C, C#, Ruby, Hypertext Preprocessor (PHP), Objective-C, JavaScript, etc. However, the present disclosure is not limited thereto, and any suitable control unit, controller, control board, or processor for receiving the input from the sensor and providing signal to the output device may be utilized in the system according to embodiments of the present disclosure.

The control unit may communicate with a remote device (e.g., a smartphone, a smartwatch, a laptop). The remote device may have a customizable program to display data, set values, track history, and/or communicate with other devices.

The output device may be a speaker, a buzzer, or any suitable sound making device, and/or a vibrating device.

The speaker may be customizable (e.g., message, volume, tone, duration of sound). For example, the speaker may provide a customizable message that alerts, wakes, soothes, and/or comforts the patient.

In one embodiment, the detector, the control unit and the output device may all be included in one unit. For example, the detector, the control unit, and the output device may all be included together inside one case (e.g., housing). In another embodiment, the detector, the control unit and the output device may be separated from one another. For example, the detector may be located on and/or near the patient, and the control unit and the output device may be located further away from the patient. In another embodiment, the detector and the control unit are included together inside one case, and the output device may be located in a different place.

According to another embodiment, the system may further include a display showing the parameter detected, a memory device for recording the parameter detected throughout the night, and/or a communication part for sending the recorded information to another device, such as a computer, a smartphone, a tablet, etc. For example, the patient and/or caregiver may review the information recorded during the night, and track the severity of sleep disorder, the development of the sleep disorder, and link it to the behavior of the patient at night. The patient and/or caregiver may set the criteria for sounding the alarm according to the analysis of the recorded information.

According to one embodiment, the detector may include a unit to send the detected parameter to another device, such as a smartphone, through wireless communication. The control unit and the alarm may be implemented using the smart phone system through an app. In one embodiment, the detector may be coupled to more than one device; for example, the detector may be coupled to both the patient's smartphone and a caregiver's smartphone such that both the patient and the caregiver can receive the information about the patient's sleep status.

The system may further include a suitable power source, such as a battery pack or a battery. For example, the system may be powered by a coin cell battery, an AA battery, a AAA battery, or multiple batteries, or powered through plug into a power outlet.

The system may further include an attachment part, such as a magnet, Velcro, belt, etc., for attaching to a fixture and/or the patient.

The system according to embodiments of the present disclosure may alert a patient with sleep disorder before the patient leaves the bed. By identifying and detecting the parameters that are indicative of an injury-causing scenario in the patient's sleep, the system wakes the patient before the patient causes harm to himself/herself. For example, the system detects the screaming, shouting, and/or forceful movement of the patient, and wakes the patient while he/she is still in bed. Furthermore, the system may be customized to suit the behavior pattern of each patient to reduce or minimize false alarms.

With the system according to embodiments of the present disclosure, the patient with sleep disorder can be woken up without the involvement of a caregiver, which may allow the caregiver to have a better sleep quality at night and also give the family members peace of mind when not physically close to the patient.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Expressions such as "at least one of," when preceding a list of elements, modify the entire list of elements and do not modify the individual elements of the list. Further, the use of "may" when describing embodiments of the inventive concept refers to "one or more embodiments of the inventive concept." Also, the term "exemplary" is intended to refer to an example or illustration.

The patient alert system and/or any other relevant devices or components according to embodiments of the present invention described herein may be implemented utilizing any suitable hardware, firmware (e.g. an application-specific integrated circuit), software, or a combination of software, firmware, and hardware. For example, the various components of the patient alert system may be formed on one integrated circuit (IC) chip or on separate IC chips. Further, the various components of the patient alert system may be implemented on a flexible printed circuit film, a tape carrier package (TCP), a printed circuit board (PCB), or formed on one substrate. Further, the various components of the patient alert system may be a process or thread, running on one or more processors, in one or more computing devices, executing computer program instructions and interacting with other system components for performing the various functionalities described herein. The computer program instructions are stored in a memory which may be implemented in a computing device using a standard memory device, such as, for example, a random access memory (RAM). The computer program instructions may also be stored in other non-transitory computer readable media such as, for example, a CD-ROM, flash drive, or the like. Also, a person of skill in the art should recognize that the functionality of various computing devices may be combined or integrated into a single computing device, or the functionality of a particular computing device may be distributed across one or more other computing devices without departing from the scope of the exemplary embodiments of the present invention.

What is claimed is:

1. A system of alerting patient with sleep disorder, comprising:
    a detector for detecting a change in a parameter and
    an output device for sounding an alarm,
    wherein the parameter comprises sound, blood pressure, and movement,
    the movement comprises movement of at least one body part selected from arm, leg, and head, and
    wherein the change comprises shifting in pitch of the patient's voice, 3% or higher change in blood pressure, and change in magnitude and frequency of the movement.

2. The system of claim 1, wherein the detector comprises a motion sensor, an audio sensor, and a blood pressure sensor.

3. The system of claim 1, further comprising a control unit for deciding if the change meets a set criteria, and if the change meets the set criteria, triggering the output device to sound the alarm.

4. The system of claim 3, wherein the control unit is to adapt the set criteria according to sleep behavior of the patient.

5. The system of claim 3, wherein the control unit comprises a codable device.

6. The system of claim 1, wherein the output device is a speaker.

7. The system of claim 6, wherein the speaker is to say a customized message comprising a family member's voice; and/or phrases selected from "mom," "dad," "wake up," a phrase from a song lyric, a phrase from the Bible, and a movie line.

8. The system of claim 1, wherein the system is to communicate with a remote device.

9. A method of alerting patient with sleep disorder, the method comprising:
    detecting a change in a parameter, and
    sounding an alarm,
    wherein the parameter comprises sound, blood pressure, and movement, the movement comprises movement of at least one body part selected from arm, leg, and head, and wherein the change comprises shifting in pitch of the patient's voice, 3% or higher change in blood pressure, and change in magnitude and frequency of the movement.

10. The method of claim 9, further comprising deciding if the change meets a set criteria, and if the change meets the set criteria, sounding the alarm.

11. The method of claim 10, wherein the set criteria is adaptable to sleep behavior of the patient.

12. The method of claim 10, wherein the parameter further comprises heartbeat, and the set criteria comprises a threshold value of the heartbeat.

13. The method of claim 10, wherein the set criteria comprises a threshold value of the blood pressure.

14. The method of claim 10, further comprising detecting a time duration of the change in the parameter, and the set criteria comprises a threshold value of the time duration.

15. The method of claim 9, wherein the alarm comprises a customizable message comprising a family member's voice; and/or phrases selected from "mom," "dad," "wake up," a phrase from a song lyric, a phrase from the Bible, and a movie line.

16. The method of claim 9, further comprising establishing a reference value for the parameter for a specific patient.

17. The method of claim 9, further comprising attaching a device to the patient, wherein the device is to detect the change in the parameter and/or sound the alarm.

18. The method of claim 12, wherein the set criteria comprises 10% or higher change in heartbeat value.

19. The method of claim 10, wherein the parameter further comprises breathing frequency, and the set criteria comprises 10% or higher change in breathing frequency.

20. A system of alerting patient with sleep disorder, comprising:
   a detector for detecting a change in a parameter, and
   an output device for sounding an alarm,
   wherein the parameter comprises sound, motion, heartbeat, blood pressure, and breathing frequency, and
   wherein the change comprises change in pitch, frequency, intensity, and/or volume of a voice; change in speed and/or frequency of the motion; 10% or higher change in heartbeat value; 3% or higher change in blood pressure; and 10% or higher change in breathing frequency.

* * * * *